(12) United States Patent
Li et al.

(10) Patent No.: US 9,226,994 B2
(45) Date of Patent: Jan. 5, 2016

(54) INTERVENTION MEDICAL DEVICE AND PREPARATION THEREOF

(75) Inventors: Junfei Li, Shanghai (CN); Xi Hu, Shanghai (CN); Chengyun Yue, Shanghai (CN); Dawei Wang, Shanghai (CN); Peng Huang, Shanghai (CN); Zhirong Tang, Shanghai (CN); Qiyi Luo, Shanghai (CN); Zhaohua Chang, Shanghai (CN)

(73) Assignee: Shanghai MicroPort Medical (Group) Co., Ltd., Shanghai (CN)

( * ) Notice: Subject to any disclaimer, the term of this patent is extended or adjusted under 35 U.S.C. 154(b) by 0 days.

(21) Appl. No.: 13/703,855

(22) PCT Filed: Jun. 13, 2011

(86) PCT No.: PCT/CN2011/075648
§ 371 (c)(1),
(2), (4) Date: Jul. 29, 2013

(87) PCT Pub. No.: WO2011/157208
PCT Pub. Date: Dec. 22, 2011

(65) Prior Publication Data
US 2013/0296806 A1 Nov. 7, 2013

(30) Foreign Application Priority Data
Jun. 13, 2010 (CN) .......................... 2010 1 0201511

(51) Int. Cl.
| | | |
|---|---|---|
| *A61L 27/34* | (2006.01) | |
| *A61L 27/54* | (2006.01) | |
| *A61L 31/10* | (2006.01) | |
| *A61L 31/16* | (2006.01) | |

(52) U.S. Cl.
CPC ............... *A61L 27/34* (2013.01); *A61L 27/54* (2013.01); *A61L 31/10* (2013.01); *A61L 31/16* (2013.01); *A61L 2300/42* (2013.01)

(58) Field of Classification Search
None
See application file for complete search history.

(56) References Cited

U.S. PATENT DOCUMENTS

| | | | |
|---|---|---|---|
| 5,840,387 A | * | 11/1998 | Berlowitz-Tarrant et al. ................. 428/36.91 |
| 2007/0250159 A1 | | 10/2007 | Davis et al. |
| 2007/0298067 A1 | * | 12/2007 | Kangas ................. 424/423 |

FOREIGN PATENT DOCUMENTS

| | | |
|---|---|---|
| CN | 1726884 | 2/2006 |
| WO | WO 2007/149161 A2 | 12/2007 |
| WO | WO 2009/002984 A2 | 12/2008 |

OTHER PUBLICATIONS

Pinchuk et al. (Medical Applications of poly(styrene-block-isobutylene-block-styrene), Biomaterials (2007).*
International Search Report issued by the State Intellectual Property Office of P.R. China on Sep. 29, 2011 in connection with International Patent Application No. PCT/CN2011/075648. 5 pages.

* cited by examiner

*Primary Examiner* — Robert A Wax
*Assistant Examiner* — Melissa Mercier
(74) *Attorney, Agent, or Firm* — Hamre, Schumann, Mueller & Larson, P.C.

(57) ABSTRACT

The present invention discloses an interventional medical device and methods of making the same. At least one coating layer is disposed on the outer surface of the interventional medical device and the material of the outmost layer of the coating layer is a sulfonate group-containing polymer. In the present invention, the material of the outmost layer of the interventional medical device is a sulfonate group-containing polymer. The polymer is endowed with a same surface property as that of heparin in addition to appropriate hydrophilicity due to the presence of the sulfonate group. After the interventional medical device is implanted into the human body, a hydrophilic surface is formed on the outer surface of the interventional medical device which is also negatively charged in the body fluid. Therefore, cells can easily adhere and grow on the outer surface thereof as a result of the enhanced cell compatibility. Furthermore, due to a surface property that is the same as that of heparin, the material is provided with excellent anticoagulant properties which inhibit the thrombosis and lower down the incidence rate of post-operational complications.

16 Claims, 2 Drawing Sheets

INTERVENTION MEDICAL DEVICE AND PREPARATION THEREOF

TECHNICAL FIELD

The present invention is related to the field of a medical device, particularly, an interventional medical device and a method of making the same.

BACKGROUND

Interventional medical devices, as a rising technique in the field of medical devices in recent 20 years, play important roles in reducing patients' trauma and improving the efficacy of disease treatment. An example for such a device is represented by an interventional device applied in a variety of lumens in a human body, such as an intravascular stent, a biliary stent, an esophageal stent, an intestinal stent, a pancreatic duct stent, a urethral stent or a tracheal stent et al., and the associated interventional catheter, balloon, filter and the like. Among them, the stent exhibits a particularly outstanding performance in the field of interventional medical devices. For various vascular diseases resulted from vascular obstruction or other causes, a stent has been proven to be a relatively successful interventional medical device for long-term implantation into the blood vessel. During an operation, the stent is delivered to location of a vascular lesion for block through a delivery system and then deployed. Thus, the blocked blood vessel is enlarged by the expanded stent and the patency is maintained.

In order to improve the effect of biocompatibility and the therapeutic effect of the interventional medical device in vivo, certain part of or the entire surface of the body of these devices can be coated with drugs and/or polymers. For example, the surface of the stent can be coated with a polymer layer containing drugs. When the stent with a drug-containing layer is implanted into a human body, not only that the obstructed blood vessel can be expanded to open by the stent, but also that the drugs in the drug-containing layer can be continuously released to the pathological vascular tissue that is in contact with the drug-containing layer. Thereby, a thorough treatment can be achieved.

However, because of the complexity of the physiological constitution of the human body, there is complicated biocompatibility problem associated with the interventional medical device itself in its application in a human body. In addition, the polymer coating material on the interventional medical device will also cause same biocompatibility problem in vivo. Commonly used polymer materials at present primarily include polymethacrylates, fluoropolymers, polyethylene-based polymers or polystyrene-based polymers, which are all used for industrial applications at the beginning and have poor biocompatibility.

Hence, the interventional medical device in the prior art may cause more serious thrombosis and post-operational complications after being implanted into a human body for an extended period of time due to its poor biocompatibility.

THE CONTENT OF THE INVENTION

To solve the above technical problem, the present invention provides an interventional medical device as described in the following technical solutions:

An interventional medical device with at least one coating layer disposed on the outer surface thereof and the material of the outmost layer of said coating layer is a sulfonate group-containing polymer.

Preferably, said sulfonate group-containing polymer is a sulfonated thermoplastic elastomer.

Preferably, said sulfonated thermoplastic elastomer is a sulfonated styrene-olefin copolymer.

Preferably, said styrene-olefin copolymer is a styrene-isobutylene diblock or triblock copolymer.

Preferably, the content of the styrene in said styrene-isobutylene diblock or triblock copolymer is 25%~55% by weight.

Preferably, the degree of sulfonation of the sulfonate group-containing polymer in said outmost layer is 5%~30%.

Preferably, the degree of sulfonation of the sulfonate group-containing polymer in said outmost layer is 10%~20%.

In the interventional medical device, in the case when said coating layer is composed of multilayers, the layers other than the outmost layer contain sulfonate group-containing polymer.

Preferably, the degree of sulfonation of the sulfonate group-containing polymer in said layer other than the outmost layer is smaller than the degree of sulfonation of the sulfonate group-containing polymer in the outmost layer.

Preferably, the degree of sulfonation of the sulfonate group-containing polymer in said layer other than the outmost layer is 0%~15%.

Preferably, the degree of sulfonation of the sulfonate group-containing polymer in said layer other than the outmost layer is 5%~10%.

Preferably, at least one layer of said coating layers contains a drug.

In the interventional medical device, in the case when said drug reacts with said sulfonate group-containing polymer, then a sulfonate group-containing polymer will not be utilized as the material of the drug-containing layer. Preferably, there is at least one isolation layer without sulfonate group-containing polymer between said drug-containing layer and a coating layer of sulfonate group-containing polymer.

Preferably, said interventional medical device is a luminal stent for human body.

Preferably, said luminal stent for human body includes coronary artery stents, intracranial vascular stents, peripheral vascular stents, intraoperative stents, heart valve stents, biliary stents, esophageal stents, intestinal stents, pancreatic duct stents, urethral stents or tracheal stents, and is preferably a coronary artery stent.

In the interventional medical device provided in the present invention, the coating material for an outmost layer is a sulfonate group-containing polymer. The polymer is endowed with a same surface property as that of heparin in addition to appropriate hydrophilicity due to the presence of the sulfonate group. After the interventional medical device is implanted into the human body, as a result of the sulfonate group presented in the surface of the polymer material, said polymer material can form a thin hydrophilic film layer at the molecular level and is negatively charged in the surface thereof in the body fluid. Improved compatibility with cells is thus obtained.

Therefore, after the interventional medical device has been implanted into the human body, cells can easily adhere and grow on the cell-friendly surface of the outmost layer of the device. Furthermore, due to the same surface property as that of heparin, formation of thrombus is inhibited and the incidence rate of post-operational complications is reduced.

In addition, since the lipophilic main chain in the sulfonate group-containing polymer is compatible with the drug at the molecular level, a biological active drug can be carried in the sulfonate group-containing polymer coating layer of the present interventional medical device, and further be released slowly in a controlled manner to thereby improve the efficacy of the treatment.

The present invention provides a method of making the interventional medical device, comprising:
dissolving a sulfonated lipid-soluble thermoplastic elastomer into an organic solvent to obtain a solution of the sulfonated lipid-soluble thermoplastic elastomer;
dissolving a drug into said solution of the sulfonated lipid-soluble thermoplastic elastomer to obtain a drug-containing solution of the sulfonated lipid-soluble thermoplastic elastomer;
coating the outer surface of an interventional medical device with one or more layers of said drug-containing solution of the sulfonated lipid-soluble thermoplastic elastomer.

A sulfonate group-containing polymer is prepared through further modification of a traditional lipid-soluble thermoplastic elastomer which is well known by one skilled in the art with a conventional sulfonation reaction. Said traditional lipid-soluble thermoplastic elastomer includes, but not limited to, polymethacrylates, fluoropolymers, polyethylene-based thermoplastic elastomers and/or polystyrene-based thermoplastic elastomer, and is preferably a polystyrene-based thermoplastic elastomer, more preferably a poly(styrene-isobutylene) elastomer.

Significant properties of the sulfonate group-containing polymer obtained through sulfonation of the traditional lipid-soluble thermoplastic elastomer include good lipid-solubility and a certain extent of hydrophilicity. The hydrophilic branched chain of the polymer confer good compatibility with cells to the device, while the hydrophobic main chain of the polymer can achieve compatibility at a molecular level with the also-lipid-soluble drug so that the embedding of the drug during the preparation of the interventional medical device is benefited and a control towards the drug release is gained. Meanwhile, good physical and mechanical properties and adhesive properties of these thermoplastic elastomers can prevent cracking and peeling off of the coating layer when they are applied on the interventional medical device.

The organic solvent used in the present invention includes, but not limited to, tetrahydrofuran, chlorinated alkanes, toluene and/or alcohols, and is preferably a mixture of tetrahydrofuran and an alcohol, more preferably a 2:1 mixture of tetrahydrofuran and ethanol.

According to the present invention, a preferable method for preparing the sulfonated thermoplastic elastomer comprises:
dissolving a lipid-soluble thermoplastic elastomer into an organic solvent to obtain a mixed solution;
adding to said mixed solution a sulfonating agent and reacting in a heated condition to obtain a reaction mixture;
adding to said reaction mixture an alcohol to obtain a sulfonated lipid-soluble thermoplastic elastomer;
purifying said sulfonated lipid-soluble thermoplastic elastomer.

The sulfonating agent used in the present invention includes but not limited to, concentrated sulfuric acid, sulfur trioxide, chlorosulfonic acid, an acyl sulfonate, a product from acyl chloride and sulfuric acid reaction, or a product from anhydride and sulfuric acid reaction. The above sulfonating agent can be bought commercially or prepared in the lab. The preferable sulfonating agent used in the present invention is chlorosulfonic acid, acyl sulfonate, or the product between an acyl chloride or an anhydride and sulfuric acid reaction. The purpose of adding alcohol to the sulfonation reaction in the present invention is to react with the excess sulfonating agent and thereby to terminate the reaction. The alcohol used in the present invention is well-known for terminating reaction in the field, including but not limited to, methanol, ethanol and/or propanol, and is preferably propanol and more preferably isopropanol. The sulfonation reaction is conducted at a temperature controlled between 20~80° C. and preferably between 30~60° C., for a period of time of 1~24 h, preferably 3~12 h.

The degree of sulfonation of the sulfonated lipid-soluble thermoplastic elastomer used in the present invention is preferably less than 20%. The degree of sulfonation of a lipid-soluble thermoplastic elastomer (i.e. the content of the sulfonate group in the lipid-soluble thermoplastic elastomer) has a great impact on the physical property of the material. Taking poly(styrene-isobutylene) thermoplastic elastomer as an example, the degree of sulfonation of more than 50% will cause the material losing its elasticity and film-forming property, and at the degree of sulfonation which is more than 30%, the material will have insufficient strength and poor adhesion. It has been proven experimentally that when a stent is coated with a sulfonated lipid-soluble thermoplastic elastomer having a degree of sulfonation of less than 20%, the coating layer thereon will not crack nor peel off and have desired physical properties. Therefore, the degree of sulfonation of the sulfonated lipid-soluble thermoplastic elastomer of the present invention is preferably 5%.

According to the present invention, a drug is added to the obtained solution of the sulfonated lipid-soluble thermoplastic elastomer and completely dissolved therein. The drug used in the present invention is an active drug well-known by a skilled in the art, including but not limited to, anticoagulants, anti-cancer drugs, microbial immunosuppressants, hormones and other anti-restenosis drugs for blood vessel, and is preferably rapamycin.

According to the present invention, the desired drug-containing interventional medical device can be prepared by coating on the outer surface of the interventional medical device one or more layers of the drug-containing solution of the sulfonated lipid-soluble thermoplastic elastomer after said drug-containing solution of the sulfonated lipid-soluble thermoplastic elastomer has been obtained.

The interventional medical device prepared according to the method of the present invention includes, for example, a luminal stent used within a human body, including but not limited to, an intravascular stent, an esophageal stent and a biliary stent, and is preferably a cardiovascular stent which includes but not limited to a flexible bare-metal stent. In order to improve the adhesion force of the sulfonated lipid-soluble thermoplastic elastomer on the stent, said cardiovascular stent can be a flexible metal stent bearing pores formed through an acid/alkali corrosion process and/or having an underlayer coated on the surface thereof.

The way for coating used in the present invention is a coating technique well-known by a skilled in the art, including but not limited to, dip coating, spray coating or electrostatic coating, and is preferably spray coating.

Compared to the prior art, the drug-containing interventional medical device prepared according to the method of the present invention has an outer surface coating layer which is made of the sulfonated lipid-soluble thermoplastic elastomer having both lipophilic and hydrophilic properties. With the lipophilicity, the coating layer on the drug-containing interventional medical device achieves compatibility with the drug at the molecular level which provides the device with the ability to carry the bioactive drug and to slowly release it in a controlled manner. On the other hand, with the hydrophilicity, the coating layer on the drug-containing interventional medical device is endowed with the same surface property as that of heparin. In the body fluid, this can provide not only a hydrophilic surface at the outer surface, but also a negatively charged outer surface for the drug-containing interventional medical device. Improved compatibility with cells is thus obtained.

Therefore, the drug-containing interventional medical device prepared according to the method of the present invention can carry a drug and release it in a controlled manner. Not only this, after the interventional medical device has been implanted into a human body, a cell-friendly layer can be formed at the outmost layer thereof on which vascular endothelial cells can easily adhere and grow. As a result, the endothelialization of the blood vessel is promoted and late thrombosis is inhibited.

The present invention further provides a method of making the interventional medical device, comprising:

dissolving a lipid-soluble thermoplastic elastomer into an organic solvent to obtain a solution of the lipid-soluble thermoplastic elastomer;

dissolving a drug into said solution of the lipid-soluble thermoplastic elastomer to obtain a drug-containing solution of the lipid-soluble thermoplastic elastomer;

coating the outer surface of a interventional medical device with one or more layers of said drug-containing solution of the lipid-soluble thermoplastic elastomer;

dissolving the sulfonated lipid-soluble thermoplastic elastomer into an organic solvent to obtain a solution of the sulfonated lipid-soluble thermoplastic elastomer;

coating the outer surface of said stent coated with a drug-containing layer with one or more layers of said solution of the sulfonated lipid-soluble thermoplastic elastomer to obtain a drug-containing interventional medical device.

According to the present invention, the interventional medical device is first coated with one or more layers of the drug-containing lipid-soluble thermoplastic elastomer as a drug-loaded coating layer, and then coated with the sulfonated lipid-soluble thermoplastic elastomer on the outmost surface thereof as a cell-friendly layer.

To prevent the sulfonated lipid-soluble thermoplastic elastomer to react, when it is used as a drug-loaded coating layer, with certain drugs, one step is further included in the invention before coating the outer surface of said interventional medical device coated with a drug-containing layer with one or more layers of said solution of the sulfonated lipid-soluble thermoplastic elastomer, which is:

coating the outer surface of said interventional medical device coated with a drug-containing layer with one or more layers of said solution of the lipid-soluble thermoplastic elastomer.

According to the present invention, one or more layers of the lipid-soluble thermoplastic elastomer containing no drug is thus provided as an isolation layer between the drug-loaded coating layer (a drug-containing coating layer of the lipid-soluble thermoplastic elastomer) and the cell-friendly layer (a coating layer of the sulfonated lipid-soluble thermoplastic elastomer). The drug and the coating layer of the sulfonated lipid-soluble thermoplastic elastomer are separated by the isolation layer and the reaction between them is prevented.

Compared to the prior art, the drug-containing interventional medical device prepared according to the method of the present invention has a cell-friendly layer as the outmost layer, and can promote the endothelialization of the blood vessel and inhibit thrombosis.

BRIEF DESCRIPTION OF THE FIGURES

To better illustrate the examples in the present invention or the technical solutions in the prior art, the figures used in the Examples or the technical solutions will be briefly described as follows. It is obvious that the figures below represent only a few of the examples recorded in the application and a skilled in the art can obtain other figures according to what have been shown here without paying any inventive effort.

DETAILED DESCRIPTION OF THE INVENTION

The present invention provides an interventional medical device on which a hydrophilic and sulfonate group-containing polymer is used as the material of the outmost polymer coating layer. After the implantation, a cell-friendly layer that is compatible with cells can be formed on the outer surface of the interventional medical device so that cells can easily adhere and grow on the surface thereof. In addition, said surface has a same surface property as that of heparin, and can inhibit thrombosis and lower down the risks of complication.

Above is the gist of the present application. For a skilled in the art to better understand the technical solutions in the application, technical solutions in the application will be described thoroughly hereinafter in more detail with reference to the figures therein. Clearly, the examples described herein represent only a few examples instead of all of the examples of the application. All the other examples obtained based on the examples of the present application by one ordinary skilled in the art without paying any inventive effort are deemed to fall into the scope of protection of the present application.

EXAMPLES

Example 1

Figure 1:
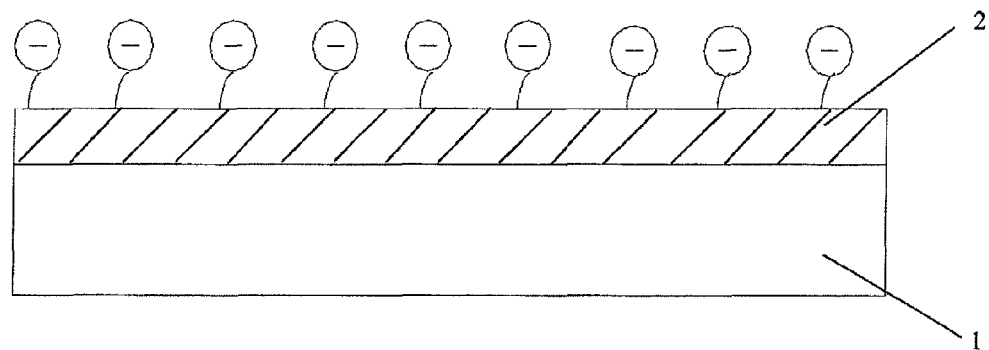
FIG. 1 is a schematic diagram showing the structure of an interventional medical device provided in Example 1 of the present invention.

FIG. 1 is a schematic diagram showing the structure of an interventional medical device provided in Example 1 of the present invention.

As shown in FIG. 1, the interventional medical device comprises stent body 1, and coating layer 2 which is disposed on the outer surface of stent body 1, wherein the material of coating layer 2 is a sulfonate group-containing polymer.

In this example of the application, the sulfonate group-containing polymer used in coating layer 2 includes but not limited to a sulfonated thermoplastic elastomer, and is preferably a sulfonated styrene-olefin copolymer, more preferably a sulfonated styrene-isobutylene diblock or triblock copolymer with a styrene content of 25~55% by weight. The sulfonated thermoplastic elastomer can further be other copolymers well-known by a skilled in the art.

In this example of the application, since the amount of the sulfonate group incorporated into the copolymer (i.e. the content of the sulfonate group) has a great impact on the properties of the copolymer material, the degree of sulfonation of the sulfonate group-containing polymer used in coating layer 2 is preferably 5%~30%. The amount of the sulfonate group incorporated is usually represented by the degree of sulfonation (i.e. the percentage of the benzene ring being sulfonated). Taking poly(styrene-butylene) copolymer as an example, at the degree of sulfonation which is more than 50%, the material will lose its elasticity and film-forming property, and at the degree of sulfonation which is more than 30%, the material will have insufficient strength and poor adhesion. Hence in the example of the present application, the degree of sulfonation of 5%~30% is selected for the sulfonate group-containing polymer, as in this range, the coating layer formed after the sulfonate group-containing polymer is coated on stent body 1 will not crack or peel off easily under stress, and has desired physical properties. More preferably, the degree of sulfonation of the sulfonate group-containing polymer used in coating layer 2 in the example of the application is 10%~20%.

Example 2

Figure 2:
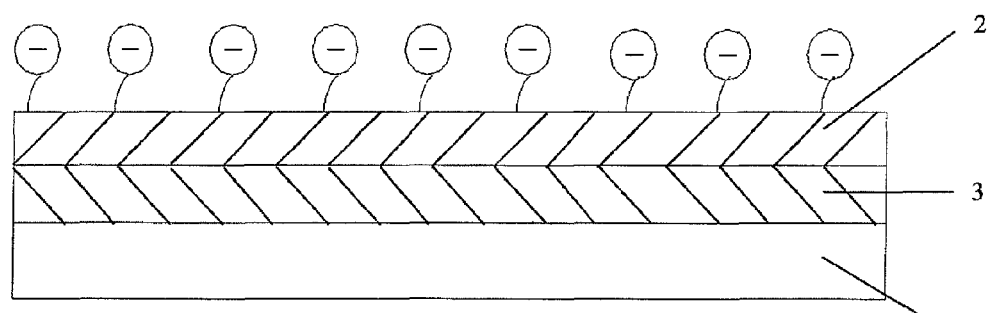
FIG. 2 is a schematic diagram showing the structure of an interventional medical device provided in Example 2 of the present invention.

FIG. 2 is a schematic diagram showing the structure of an interventional medical device provided in Example 2 of the present invention.

As shown in FIG. 2, the interventional medical device comprises stent body 1, and outmost coating layer 2 and inner coating layer 3 which are both coated on the outer surface of stent body 1, wherein the material of outmost coating layer 2 is a sulfonate group-containing polymer with a degree of sulfonation of 5%~30%, more preferably 10%~20%.

Inner coating layer 3 can be inorganic, organic or a conventional polymer coating layer, and can also be a sulfonate group-containing polymer coating layer. In the case when inner coating layer 2 is made of sulfonate group-containing polymer, because inner coating layer 3 and outmost coating layer 2 are in different environment and have different requirements upon the property of their own material, the material used for inner coating layer 3 should desirably have stronger adhesion and so the degree of sulfonation of the sulfonate group-containing polymer in inner coating layer 3 should be smaller than the degree of sulfonation of the sulfonate group-containing polymer in outmost coating layer 2. In the example of the present application, the degree of sulfonation of the sulfonate group-containing polymer in inner coating layer 3 is controlled under 15%, and is preferably 5~10%.

Example 3

Figure 3:
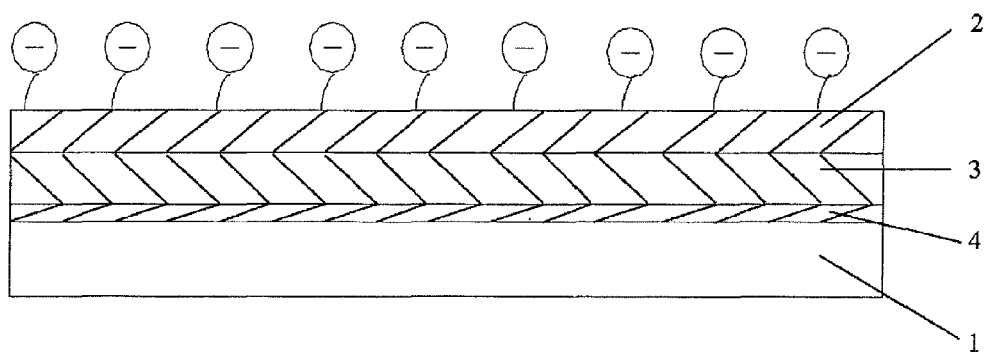
FIG. 3 is a schematic diagram showing the structure of an interventional medical device provided in Example 3 of the present invention.

FIG. 3 is a schematic diagram showing the structure of an interventional medical device provided in Example 3 of the present invention.

As shown in FIG. 3, on the foundation of Example 2, an underlayer 4 can be provided between inner coating layer 3 and stent body 1 if required.

Similar to inner coating layer 3 in Example 2, underlayer 4 can also be inorganic, organic or a conventional polymer coating layer and further a sulfonate group-containing polymer coating layer. In the case when underlayer 4 is made of a sulfonate group-containing polymer, the degree of sulfonation of the sulfonate group-containing polymer in underlayer 4 is controlled under 15%, and is preferably 5~10%.

Example 4

In this example of the application, multiple coating layers are disposed on the outer surface of stent body 1, wherein as the material of the outmost layer, a sulfonate group-containing polymer is used, and the degree of sulfonation of the sulfonate group-containing polymer used in outmost coating layer 2 is 5%~30%, more preferably 10%~20%, and at least one of the multiple coating layers contains a drug.

Figure 4:
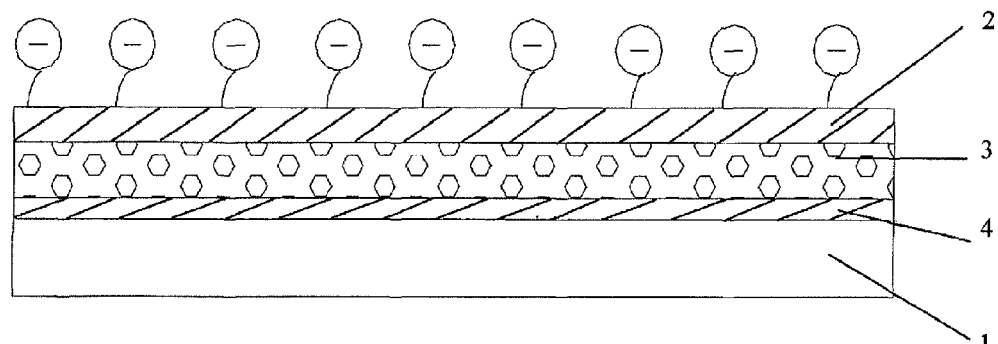
FIG. 4 is a schematic diagram showing the structure of a drug-containing interventional medical device provided in Example 4 of the present invention.

As shown in FIG. 4, in this example, there are three coating layers on the outer surface of stent 1, namely outmost coating layer 2, inner coating layer 3 and underlayer 4, wherein a drug is contained in inner coating layer 3.

Figure 5:
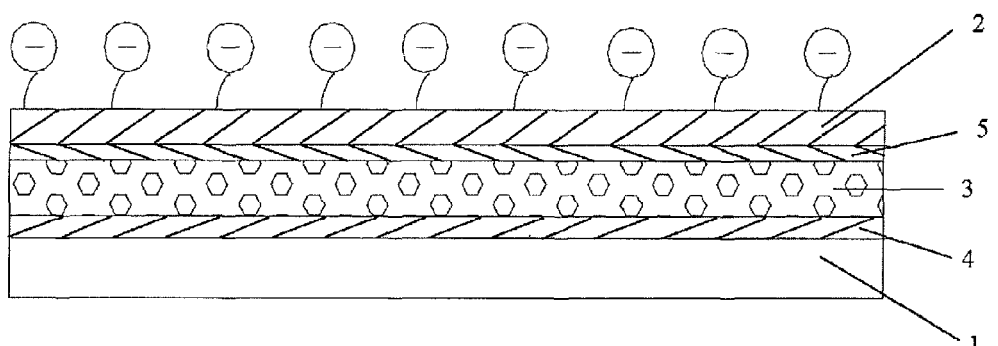
FIG. 5 is a schematic diagram showing the structure of another drug-containing interventional medical device provided in Example 4 of the present invention.

In other examples of the application, in order to prevent the reaction between certain specific drug and the sulfonate group-containing polymer in outmost coating layer 2, an isolation layer 5 is disposed between the drug-containing inner coating layer and the outmost coating layer as shown in FIG. 5, and the drug-containing inner coating layer 3 is made of materials without a sulfonate group-containing polymer.

Example 5

Synthesis of Polystyrene-Based Thermoplastic Elastomer with the Degree of Sulfonation of 5%

For the sulfonation and characterization method of poly (styrene-isobutylene), please refer to:

"sulfonation and characterization of poly(styrene-isobutylene-styrene) triblock copolymer at high ion-exchange capacities", Yossef A. Elabda, Eugene Napadensky, Polymer 45, 3038 (2004) 3037-3043.

To a 25 mL conical flask are added sequentially 12 mL of dichloromethane and 4.25 mL (0.045 mol) of acetic anhydride. The mixture is stirred in an ice bath at 0-5° C. for 10 min, followed by the addition of 1.63 mL (0.03 mol) of concentrated sulfuric acid under stirring. Keep stirring at 0-5° C. for about 10 min until a clear reaction solution is obtained. The conical flask is then taken out of the ice bath and allowed to return to room temperature for later use.

To a 250 mL three-necked flask are added 10 g of poly (styrene-isobutylene) thermoplastic elastomer (with a styrene content of 37.2 mol %) and 100 mL of dichloromethane. Raise the temperature to about 40° C. to make sure that the reactant is completely dissolved and then 1.5 mL of the above reaction solution is added slowly and the reaction is kept at 40° C. for about 5 h. Then, the reaction is terminated by slowly adding 20 mL of isopropanol.

Example 6

Synthesis of poly(styrene-isobutylene) thermoplastic elastomer with the degree of sulfonation of 25%

To a 25 mL conical flask are added sequentially 12 mL of dichloromethane and 4.25 mL (0.045 mol) of acetic anhydride. The mixture is stirred in an ice bath at 0-5° C. for 10 min, followed by the addition of 1.63 mL (0.03 mol) of concentrated sulfuric acid under stirring. Keep stirring at 0-5° C. for about 10 min until a clear reaction solution is obtained. The conical flask is then taken out of the ice bath and warmed to room temperature for later use.

To a 250 mL three-necked flask are added 10 g of poly (styrene-isobutylene) thermoplastic elastomer (with a styrene content of 37.2 mol %) and 100 mL of dichloromethane. Raise the temperature to about 40° C. to make sure that the reactant is completely dissolved and then 7.5 mL of the above reaction solution is added slowly and the reaction is kept at 60° C. for about 12 h. Then, the reaction is terminated by slowly adding 20 mL of isopropanol.

Example 7

Purification

Products from Example 5 and Example 6 are collected and dried naturally in a fume hood. Then, each product is added with 50 mL of tetrahydrofuran and stirred at room temperature till the product is completely dissolved followed by a filtration. After the filtration, a proper amount of ethyl acetate is added while stirring and the polymer is precipitated in the form of fine granule. Then filtrate. The fine granular polymer filtered is laid evenly on a glass dish and naturally air dried for 2 h until the granules stick to each other to form a large piece of film. Then the resulted film is extracted with ethanol for multiple times, 5 min each time, and then quickly washed with water. After most of the water is drained out, the film is put into a vacuum oven to be further dried.

Example 8

Preparation of a Drug-Containing Stent

To 0.1 g of ethylene-vinyl alcohol copolymer is added 2 mL of N,N-dimethylacetamide. Said copolymer is dispersed homogeneously at 80° C. and then the mixture is sprayed onto the surface of the stent. The stent is placed into a vacuum oven at 60° C. to cure for 24 h.
To 0.2 g of sulfonated thermoplastic elastomer with the degree of sulfonation of 10% is added 10 mL of tetrahydrofuran. The mixture is stirred at room temperature until the elastomer is completely dissolved and added with 0.1 g of rapamycin which is then homogeneously dispersed at room temperature. Take the above stent and spray the dispersion liquid onto the surface of the stent. The stent is then placed into a vacuum oven at 40° C. to cure for 24 h.
To 0.1 g of sulfonated thermoplastic elastomer with a degree of sulfonation of 10% is added 5 mL of a mixture solution of tetrahydrofuran and ethanol (2:1). The mixture is stirred at room temperature until the elastomer is completely dissolved. Take the above stent and through spray coating technique the surface of the stent is coated with the obtained solution. The stent is then placed into a vacuum oven and dried under reduced pressure for 48 h.

Example 9

Preparation of a Drug-containing Stent

In 30 mL of tetrahydrofuran, 0.2 g of poly(styrene-isobutylene) thermoplastic elastomer and 0.1 g of sulfonated thermoplastic elastomer with the degree of sulfonation of 15% are dissolved completely under stirring at room temperature. Then, 0.1 g of rapamycin is added and dispersed homogeneously at room temperature. Take the above stent and spray the dispersion liquid onto the surface of the stent. The stent is then placed into a vacuum oven at 40° C. and dried under reduced pressure for 48 h.

Example 10

Preparation of a Drug-Containing Stent

In 10 mL of tetrahydrofuran, 0.1 g of poly(styrene-isobutylene) thermoplastic elastomer and 0.1 g of sulfonated thermoplastic elastomer with a degree of sulfonation of 15% are dissolved completely under stirring at room temperature. Then, 0.1 g of paclitaxel is added and dispersed homogeneously at room temperature. Take the above stent and spray the dispersion liquid onto the surface of the stent. The stent is then placed into a vacuum oven at 40° C. to cure for 48 h.
To 0.1 g of sulfonated thermoplastic elastomer with a degree of sulfonation of 25% is added 5 mL of a mixture solution of tetrahydrofuran and ethanol (2:1). The mixture is stirred at room temperature until the elastomer is completely dissolved. Take the above stent and through spray coating technique the surface of the stent is coated with the obtained solution. The stent is then placed into a vacuum oven and dried under reduced pressure for 48 h.

Example 11

Preparation of a Drug-Containing Stent

To 0.1 g of ethylene-vinyl alcohol copolymer is added 2 mL of N,N-dimethylacetamide. Said copolymer is dispersed homogeneously at 80° C. and then the mixture is sprayed onto the surface of the stent. The stent is placed into a vacuum oven at 60° C. to cure for 24 h.
To 0.3 g of sulfonated thermoplastic elastomer with the degree of sulfonation of 10% is added 30 mL of tetrahydrofuran. The mixture is stirred at room temperature until the elastomer is completely dissolved and added with 0.1 g of paclitaxel which is then homogeneously dispersed at room temperature. Take the above stent and spray the dispersion liquid onto the surface of the stent. The stent is then placed into a vacuum oven at 40° C. and dried under reduced pressure for 48 h.

Example 12

Preparation of a Drug-Containing Stent

To 0.1 g of poly(styrene-isobutylene) thermoplastic elastomer is added 10 mL of tetrahydrofuran. The mixture is stirred at room temperature until the elastomer is completely dissolved and added with 0.1 g of rapamycin which is then homogeneously dispersed at room temperature. Take the above stent and spray the dispersion liquid onto the surface of the stent. The stent is then placed into a vacuum oven at 40° C. to cure for 24 h.
To 0.1 g of sulfonated thermoplastic elastomer with a degree of sulfonation of 25% is added 10 mL of a mixture solution of tetrahydrofuran and ethanol (2:1). The mixture is stirred at room temperature until the elastomer is completely dissolved. Take the above stent and through spray coating technique the surface of the stent is coated with the obtained solution. The stent is then placed into a vacuum oven and dried under reduced pressure for 48 h.

Example 13

Preparation of a Drug-Containing Stent

To 0.1 g of sulfonated poly(styrene-isobutylene) elastomer with a degree of sulfonation of 5% is added 10 mL of tetrahydrofuran. The mixture is stirred at room temperature until the elastomer is completely dissolved, and added with 0.1 g of rapamycin which is then homogeneously dispersed at room temperature. Take the above stent and spray the dispersion liquid onto the surface of the stent. The stent is then placed into a vacuum oven at 40° C. to cure for 24 h.

To 0.1 g of sulfonated thermoplastic elastomer with a degree of sulfonation of 5% is added 10 mL of a mixture solution of tetrahydrofuran and ethanol (2:1). The mixture is stirred at room temperature until the elastomer is completely dissolved. Take the above stent and through spray coating technique the surface of the stent is coated with the obtained solution. The stent is then placed into a vacuum oven and dried under reduced pressure for 48 h.

Example 14

Preparation of a Drug-Containing Stent

To 0.1 g of sulfonated poly(styrene-isobutylene) elastomer with a degree of sulfonation of 5% is added 10 mL of tetrahydrofuran. The mixture is stirred at room temperature until the elastomer is completely dissolved, and added with 0.1 g of rapamycin which is then homogeneously dispersed at room temperature. Take the above stent and spray the dispersion liquid onto the surface of the stent. The stent is then placed into a vacuum oven at 40° C. to cure for 24 h.

To 0.1 g of sulfonated thermoplastic elastomer with a degree of sulfonation of 25% is added 10 mL of a mixture solution of tetrahydrofuran and ethanol (2:1). The mixture is stirred at room temperature until the elastomer is completely dissolved. Take the above stent and through spray coating technique the surface of the stent is coated with the obtained solution. The stent is then placed into a vacuum oven and dried under reduced pressure for 48 h.

Figure 6:
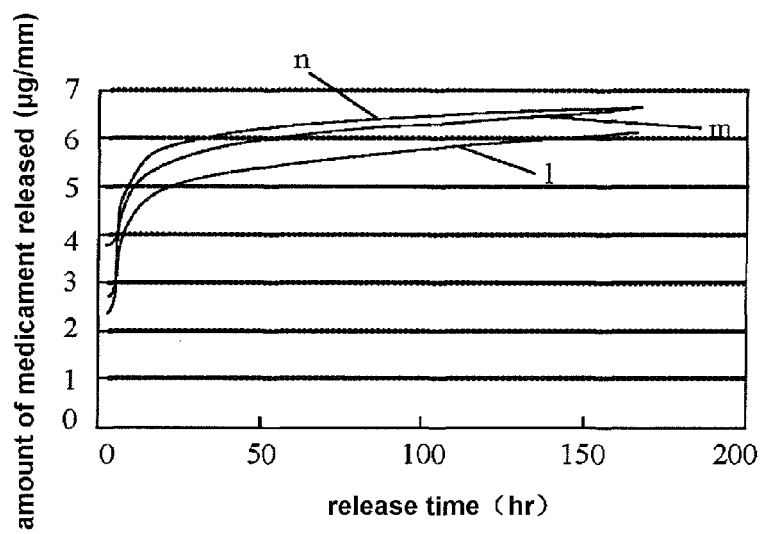
FIG. 6 shows the comparison between polymers with or without sulfonate group, in their performance in the drug release control.

FIG. 6 shows the comparison between styrene-isobutylene polymer which contains sulfonate group and styrene-isobutylene polymer which does not contain sulfonate group, in their performance in the release control of the drug, rapamycin. In the figure, curve 1 is from the polymer with no sulfonate group; curve n is from the sulfonate group-containing polymer with a degree of sulfonation of 5% (Example 13); curve m is from the sulfonate group-containing polymer with a degree of sulfonation of 25% (Example 14). As can be seen from the figure, the coating layer of the sulfonate group-containing polymer on the drug-containing stent can not only carry a bioactive drug, but also release the drug in a controlled manner. Therefore, a therapeutic effect is achieved.

The above examples are only used to help understand the method and the gist of the present invention. It should be pointed out that for those skilled in the art, various improvements and modifications can be made without departing from the principle of the invention. These improvements and modifications also fall into the scope of protection of the claims in the present invention.

The invention claimed is:

1. An interventional medical device, comprising:
    a stent body; and
    at least one coating layer disposed on an outer surface of the stent body,
    wherein the material of the outmost layer of said coating layer is a sulfonate group-containing polymer, and
    wherein the degree of sulfonation of the sulfonate group-containing polymer in said outmost layer is 5% or more but less than 20%.

2. The interventional medical device according to claim 1, wherein said sulfonate group-containing polymer is a sulfonated thermoplastic elastomer.

3. The interventional medical device according to claim 2, wherein said sulfonated thermoplastic elastomer is a sulfonated styrene-olefin copolymer.

4. The interventional medical device according to claim 3, wherein said styrene-olefin copolymer is a styrene-isobutylene diblock or triblock copolymer.

5. The interventional medical device according to claim 4, wherein the content of the styrene in said styrene-isobutylene diblock or triblock copolymer is 25%-55% by weight.

6. The interventional medical device according to claim 1, wherein the degree of sulfonation of the sulfonate group-containing polymer in said outmost layer is 10% or more but less than 20%.

7. The interventional medical device according to claim 1, wherein when said coating layer is composed of multilayers, the coating material of a layer other than the outmost layer is a sulfonate group-containing polymer.

8. The interventional medical device according to claim 7, wherein the degree of sulfonation of the sulfonate group-containing polymer in said layer other than the outmost layer is smaller than the degree of sulfonation of the sulfonate group-containing polymer in the outmost layer.

9. The interventional medical device according to claim 7, wherein the degree of sulfonation of the sulfonate group-containing polymer in said layer other than the outmost layer is 0%-15%.

10. The interventional medical device according to claim 9, wherein the degree of sulfonation of the sulfonate group-containing polymer in said layer other than the outmost layer is 5%-10%.

11. The interventional medical device according to claim 1, wherein at least one layer in said coating layer contains a drug.

12. The interventional medical device according to claim 11, wherein when said drug reacts with said sulfonate group-containing polymer, a sulfonate group-containing polymer will not be utilized as the material of the drug-containing layer.

13. The interventional medical device according to claim 12, wherein there is at least one isolation layer without sulfonate group-containing polymer between said drug-containing layer and a coating layer of sulfonate group-containing polymer.

14. The interventional medical device according to claim 11, wherein said interventional medical device is a luminal stent for human body.

15. The interventional medical device according to claim 14, wherein said luminal stent for human body includes coronary artery stents, intracranial vascular stents, peripheral vascular stents, intraoperative stents, heart valve stents, biliary stents, esophageal stents, intestinal stents, pancreatic duct stents, urethral stents or tracheal stents.

16. A method of making the interventional medical device of claim 1, comprising:
    coating the sulfonate group containing polymer on the outer surface of the stent body.

* * * * *